United States Patent [19]
Lee

[11] Patent Number: 5,713,914
[45] Date of Patent: Feb. 3, 1998

[54] SNIVEL REMOVING DEVICE

[76] Inventor: Ji Cheng Lee, No. 635, Sec. 3, Chang Her Road, Ho Mei Town, Changhua Hsien, Taiwan

[21] Appl. No.: 823,345

[22] Filed: Mar. 24, 1997

[51] Int. Cl.⁶ .................. A61F 9/00; A61M 1/00
[52] U.S. Cl. .............. 606/162; 604/321; 604/94; 604/54
[58] Field of Search .................. 604/54, 56, 73, 604/77, 94, 319–324, 141; 606/1, 162

[56] References Cited

U.S. PATENT DOCUMENTS

| | | | |
|---|---|---|---|
| 4,684,362 | 8/1987 | Holt | 604/54 |
| 5,098,386 | 3/1992 | Smith | 604/54 |
| 5,114,415 | 5/1992 | Shedlock | 604/94 |
| 5,429,599 | 7/1995 | Heinke | 604/54 |

*Primary Examiner*—Glenn K. Dawson

[57] ABSTRACT

A snivel removing device includes a housing having a stud extended upward. A valve member is engaged with the stud and includes a normally closed inlet. A nib is engaged with the valve member for engaging with the nose. A plug is slidably engaged in the housing for being moved away from the valve member and for vacuuming the bore of the housing and for drawing snivel into the bore when the valve member is squeezed to open the inlet. The snivel may thus be drawn into the housing and may be removed from the housing when the stem is disengaged from the housing.

4 Claims, 4 Drawing Sheets

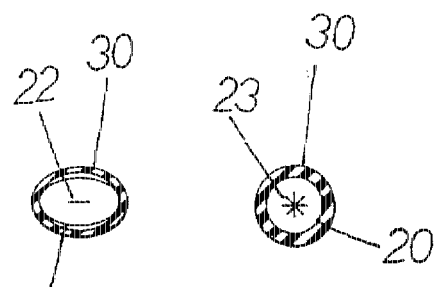
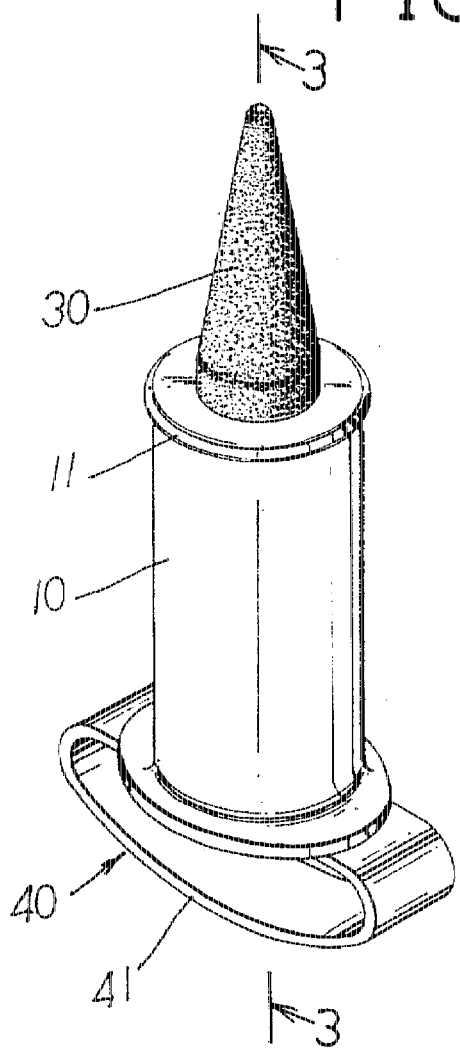
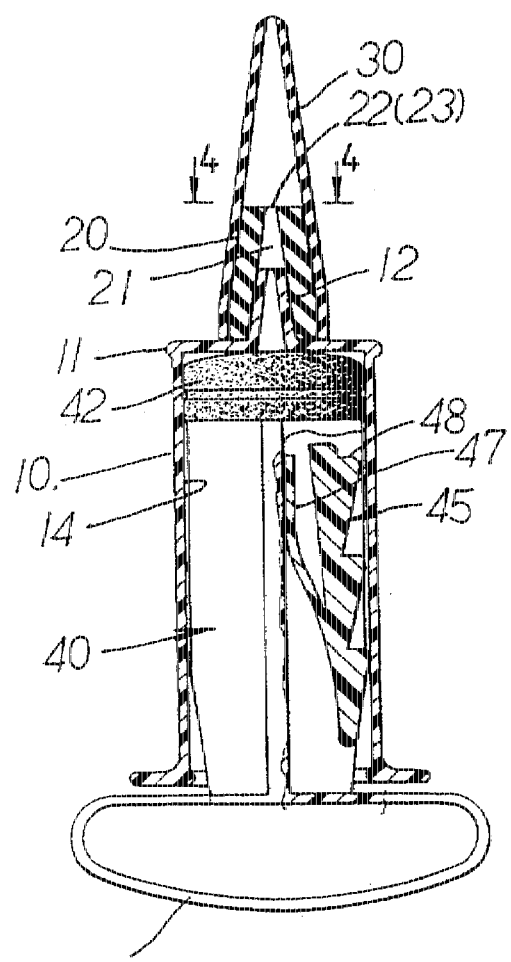

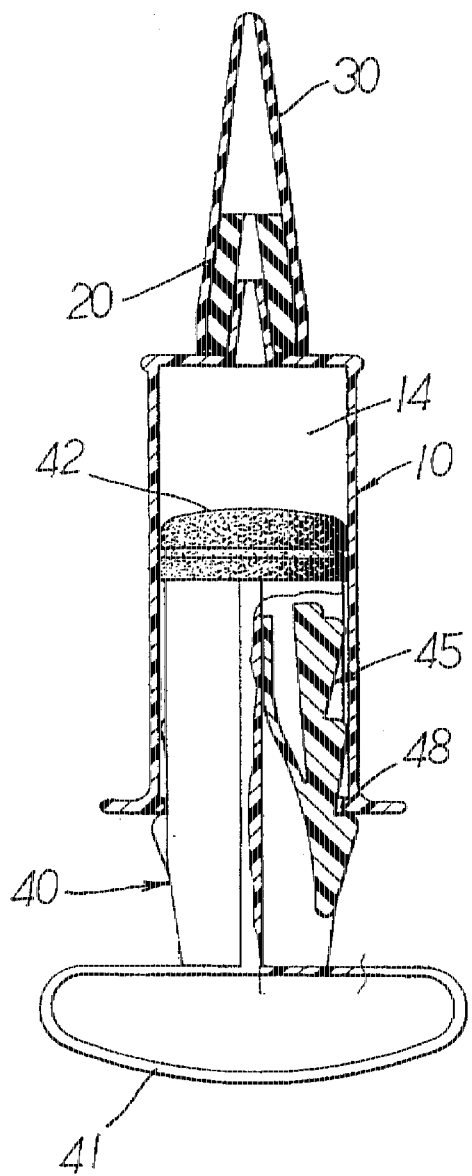
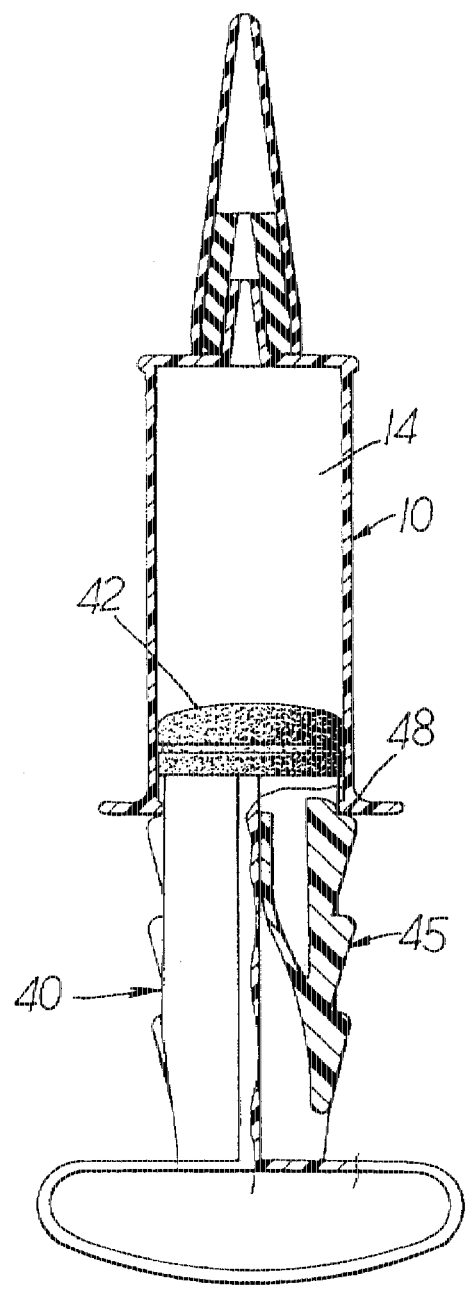
FIG. 6
FIG. 7

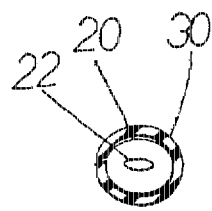
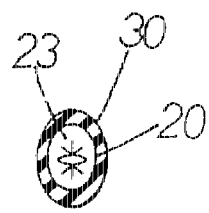
FIG.10  FIG.11
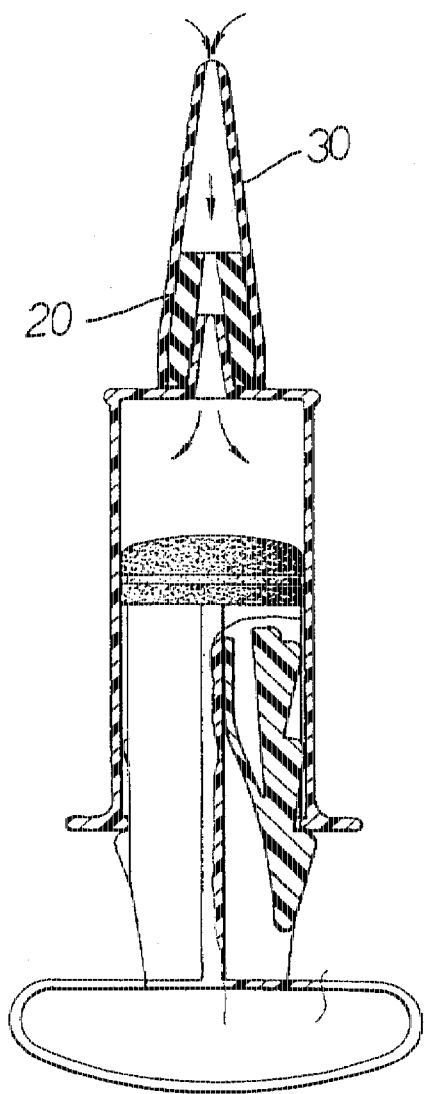
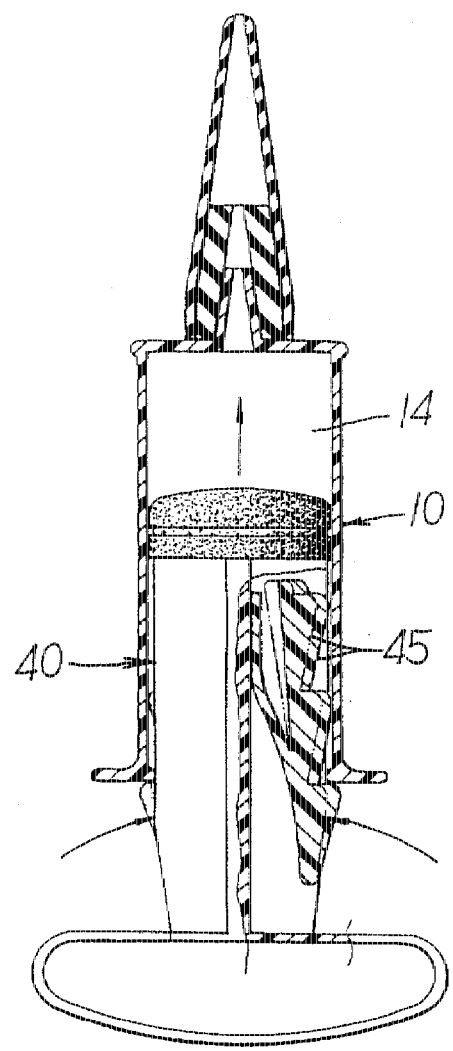
FIG.8  FIG.9

SNIVEL REMOVING DEVICE

BACKGROUND OF THE INVENTION

1. Field of the Invention

The present invention relates to a device, and more particularly to a snivel removing device.

2. Description of the Prior Art

Typical snivel removing devices comprise a flexible spherical ball member having a projection for engaging into the nose of a baby for removing the snivel from the nose of the baby. However, the snivel removed from the nose will be received in the spherical ball member and may not be easily cleaned.

The present invention has arisen to mitigate and/or obviate the afore-described disadvantages of the conventional snivel removing devices.

SUMMARY OF THE INVENTION

The primary objective of the present invention is to provide a snivel removing device including a structure for allowing the user to clean the snivel easily.

In accordance with one aspect of the invention, there is provided a snivel removing device comprising a housing including a bore and including an upper end having a stud, the stud including a hole, a valve member engaged with the stud and including a normally closed inlet, a nib engaged with the valve member for engaging with a nose of a user, a plug slidably engaged in the housing, and means for moving the plug away from the valve member and for vacuuming the bore of the housing and for drawing snivel into the bore when the valve member is squeezed to open the inlet. The snivel may thus be drawn into the bore of the housing and may be removed from the housing when the stem is disengaged from the housing.

The moving means includes a stem having an upper end secured to the plug and having a hand grip for moving the stem and the plug.

The stem includes at least one channel, the device further includes means for positioning the stem relative to the housing. The positioning means includes a stop member pivotally coupled to the stem at a pivot pin, the stop member includes at least one shoulder for engaging with the housing and for preventing the stem from being drawn into the housing.

Further objectives and advantages of the present invention will become apparent from a careful reading of a detailed description provided hereinbelow, with appropriate reference to accompanying drawings.

BRIEF DESCRIPTION OF THE DRAWINGS

FIG. 2 is a perspective view of the device;

FIG. 3 is a cross sectional view taken along lines 3—3 of FIG. 2;

FIGS. 4 and 5 are cross sectional views taken along lines 4—4 of FIG. 3;

FIGS. 6, 7, 8, and 9 are cross sectional views similar to FIG. 3, illustrating the operation of the device; and FIGS. 10 and 11 are cross sectional views similar to FIGS. 4 and 5, illustrating the operation of the device.

DETAILED DESCRIPTION OF THE PREFERRED EMBODIMENT

Figure 1:
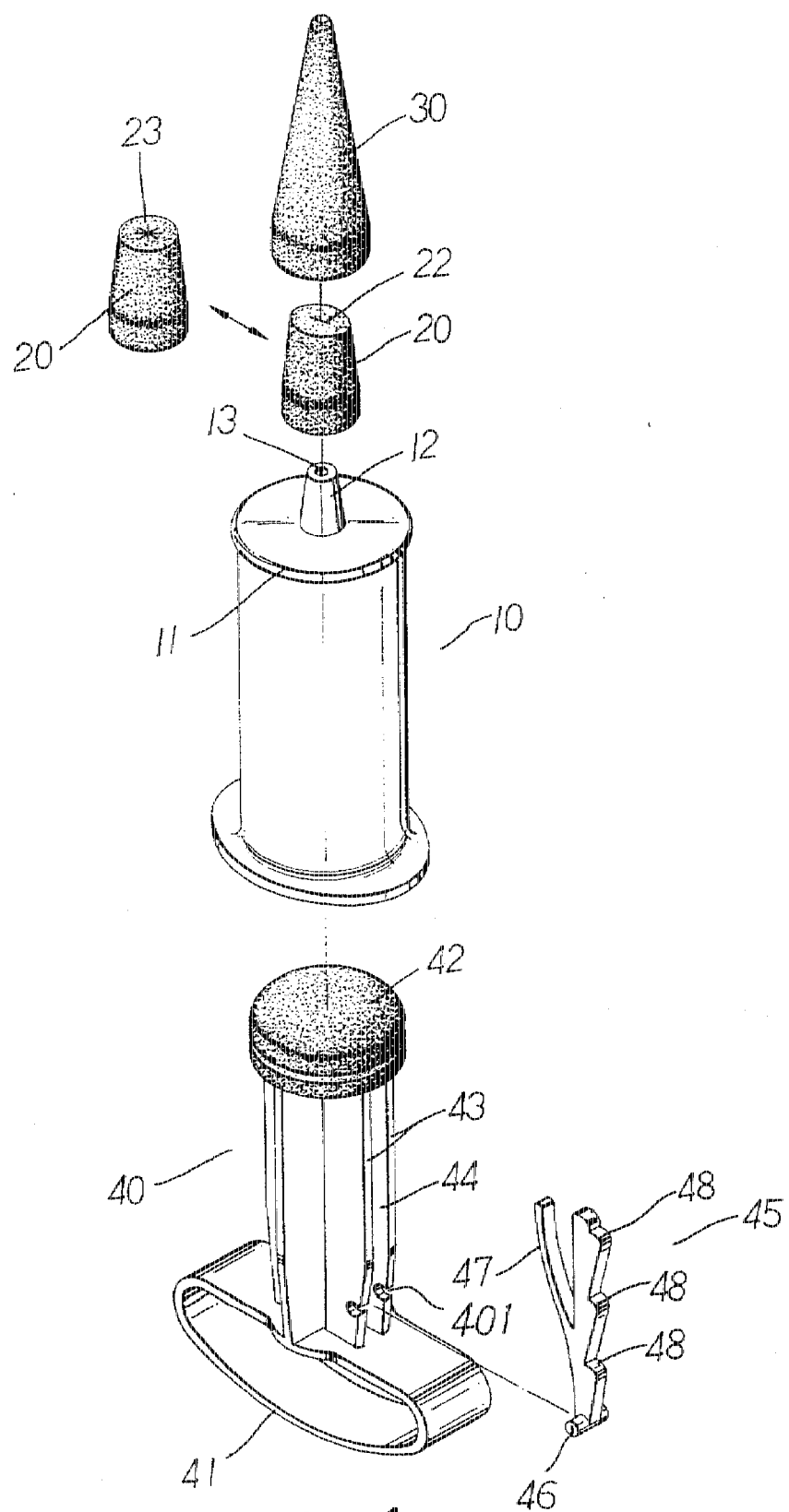
FIG. 1 is an exploded view of a snivel removing device in accordance with the present invention.

Referring to the drawings, and initially to FIGS. 1-4, a snivel removing device in accordance with the present invention comprises a cylindrical housing 10 including a stud 12 extended from the upper end 11 and having a hole 13. The housing 10 includes a bore 14 for receiving snivel. A valve member 20 is engaged on the stud 12 and includes a normally closed inlet which may be "—"-shaped 22 (FIGS. 4 and 10) or may be "*"-shaped 23 (FIGS. 5 and 11). A nib 30 is engaged on the valve member 20. The nib 30 and the valve member 20 are both made of resilient material, such as rubber for allowing the nib 30 and the valve member 20 to be squeezed and for opening the inlet 22, 23 (FIGS. 10, 11).

A stem 40 has a plug 42 secured to the upper end and slidably engaged in the housing 10 and has a hand grip 41 secured to the lower end for moving the plug 42. The stem 40 includes one or two pairs of fins 43 so as to define one or two channels 44 which may be used for receiving a biasing and stop member 45. The member 45 includes a pivot pin 46 rotatably engaged in two holes 401 of the stem 40 for allowing the member 45 to be rotated about the pivot pin 46 and for allowing the member 45 to be rotated inward of the channels 44. The member 45 includes a resilient blade 47 for engaging with the stem 40 and includes one or more shoulders 48 for engaging with the housing 10 (FIGS. 6–9) and for positioning the stem 40 relative to the housing 10.

In operation, as shown in FIGS. 6 and 7, the plug 42 may be moved away from the valve member 20 so as to vacuum the bore 14 of the housing. At this moment, the inlet 22, 23 is closed and may prevent air from entering into the bore 14. The shoulders 48 may engage with the housing 10 for preventing the stem 40 from being drawn into the housing 10. As shown in FIGS. 8 and 10, 11, when the nib 30 is engaged into the nose of the baby and when the valve member 20 is squeezed in order to open the inlet 22, 23 (FIGS. 10, 11), the snivel may thus be drawn into the bore 14 and may be removed from the housing 10 when the stem 40 is disengaged from the housing 10. As shown in FIG. 9, the stem 40 may be engaged into the housing 10 when the members 45 are moved or squeezed toward each other.

Accordingly, the device in accordance with the present invention includes a structure for allowing the user to clean the snivel easily. In addition, the device may also be easily operated.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A snivel removing device comprising:
   a housing including a bore and including an upper end having a stud, said stud including a hole,
   a valve member engaged with said stud and including a normally closed inlet,
   a nib engaged with said valve member for engaging with a nose of a user,
   a plug slidably engaged in said housing, and
   means for moving said plug away from said valve member and for vacuuming said bore of said housing and for drawing snivel into said bore when said valve member is squeezed to open said inlet.

2. A device according to claim 1, wherein said moving means includes a stem having an upper end secured to said plug and having a hand grip for moving said stem and said plug.

3. A device according to claim 2, wherein said stem includes at least one channel, said device further includes means for positioning said stem relative to said housing.

4. A device according to claim 3, wherein said positioning means includes a stop member pivotally coupled to said stem at a pivot pin, said stop member includes at least one shoulder for engaging with said housing and for preventing said stem from being drawn into said housing.

* * * * *